US00PP24678P2

(12) United States Plant Patent
Isobe

(10) Patent No.: US PP24,678 P2
(45) Date of Patent: Jul. 22, 2014

(54) ***PETUNIA* PLANT NAMED 'SUNSURF SUIKA'**

(50) Latin Name: *Petunia×hybrida*
Varietal Denomination: Sunsurf Suika

(71) Applicant: Yasuko Isobe, Shiga (JP)

(72) Inventor: Yasuko Isobe, Shiga (JP)

(73) Assignee: Suntory Flowers Limited, Tokyo (JP)

( * ) Notice: Subject to any disclaimer, the term of this patent is extended or adjusted under 35 U.S.C. 154(b) by 38 days.

(21) Appl. No.: 13/694,019

(22) Filed: Oct. 20, 2012

(51) Int. Cl.
*A01H 5/00* (2006.01)

(52) U.S. Cl.
USPC ..... Plt./356.13

(58) Field of Classification Search
CPC ..... A01H 5/02
USPC ..... Plt./356.13
See application file for complete search history.

*Primary Examiner* — Kent L Bell
(74) *Attorney, Agent, or Firm* — C. A. Whealy

(57) ABSTRACT

A new and distinct cultivar of *Petunia* plant named 'Sunsurf Suika', characterized by its compact, mounding to trailing plant habit; vigorous growth habit; freely branching habit; early and freely flowering habit; long flowering period; large light red purple-colored flowers with broad and dark yellow green-colored margins and darker red purple-colored venation; and good garden performance.

1 Drawing Sheet

Botanical designation: *Petunia×hybrida*.
Cultivar denomination: 'SUNSURF SUIKA'.

BACKGROUND OF THE INVENTION

The present invention relates to a new and distinct cultivar of *Petunia* plant, botanically known as *Petunia×hybrida* and hereinafter referred to by the name 'Sunsurf Suika'.

The new *Petunia* plant is a product of a planned breeding program conducted by the Inventor in Higashiomi, Shiga, Japan. The objective of the breeding program is to create new compact, freely branching and freely flowering *Petunia* plants with mounding habit and attractive flower coloration.

The new *Petunia* plant originated from a cross-pollination made by the Inventor in January, 2010 in Higashiomi, Shiga, Japan of a proprietary selection of *Petunia×hybrida* identified as code name Px5306-02, not patented, as the female, or seed, parent with a proprietary selection of *Petunia×hybrida* identified as code name Px5313-02, not patented, as the male, or pollen, parent. The new *Petunia* plant was discovered and selected by the Inventor as a single flowering plant within the progeny of the stated cross-pollination in a controlled greenhouse environment in Higashiomi, Shiga, Japan in November, 2010.

Asexual reproduction of the new *Petunia* plant by terminal cuttings in a controlled greenhouse environment in Higashiomi, Shiga, Japan since November, 2010 has shown that the unique features of this new *Petunia* plant are stable and reproduced true to type in successive generations.

SUMMARY OF THE INVENTION

Plants of the new *Petunia* have not been observed under all possible environmental conditions and cultural conditions. The phenotype may vary somewhat with variations in environmental conditions such as temperature and light intensity without, however, any variance in genotype.

The following traits have been repeatedly observed and are determined to be the unique characteristics of 'Sunsurf Suika'. These characteristics in combination distinguish 'Sunsurf Suika' as a new and distinct *Petunia* plant:

1. Compact, mounding to trailing plant habit.
2. Vigorous growth habit.
3. Freely branching habit.
4. Early and freely flowering habit.
5. Long flowering period.
6. Large light red purple-colored flowers with broad and dark yellow green-colored margins and darker red purple-colored venation.
7. Good garden performance.

Plants of the new *Petunia* can be compared to plants of the female parent selection. Plants of the new *Petunia* differ primarily from plants of the female parent selection in the following characteristics:

1. Plants of the new *Petunia* are more trailing than and not as upright as plants of the female parent selection.
2. Plants of the new *Petunia* have smaller flowers than plants of the female parent selection.
3. Plants of the new *Petunia* and the female parent selection differ in flower color as plants of the female parent selection have light pink-colored flowers with green-colored margins.

Plants of the new *Petunia* can be compared to plants of the male parent selection. Plants of the new *Petunia* differ primarily from plants of the male parent selection in the following characteristics:

1. Plants of the new *Petunia* have larger flowers than plants of the male parent selection.
2. Plants of the new *Petunia* and the male parent selection differ in flower color as plants of the male parent selection have white-colored flowers with green-colored margins.

Plants of the new *Petunia* can also be compared to plants of the *Petunia* 'BHTUN31501', disclosed in U.S. Plant Pat. No. 21,649. In side-by-side comparisons conducted in Higashiomi, Shiga, Japan, plants of the new *Petunia* and 'BHTUN31501' differed primarily in the following characteristics:

1. Plants of the new *Petunia* were more compact than plants of 'BHTUN31501'.
2. Plants of the new *Petunia* had shorter internodes than plants of 'BHTUN31501'.
3. Plants of the new *Petunia* had smaller leaves with shorter petioles than plants of 'BHTUN31501'.
4. Plants of the new *Petunia* were more freely flowering than plants of 'BHTUN31501'.
5. Plants of the new *Petunia* had larger flowers than plants of 'BHTUN31501'.
6. Petal apices of plants of the new *Petunia* were mucronate in shape whereas petal apices of plants of 'BHTUN31501' were broadly acute in shape.
7. Petals of plants of the new *Petunia* were coarse and bullate in texture whereas petals of plants of 'BHTUN31501' were smooth in texture.
8. Plants of the new *Petunia* and 'BHTUN31501' differed in flower color as plants of 'BHTUN31501' had dark red purple-colored flowers with green-colored margins and dark violet-colored centers.
9. Plants of the new *Petunia* had longer and thicker peduncles than plants of 'BHTUN31501'.

BRIEF DESCRIPTION OF THE PHOTOGRAPHS

The accompanying colored photographs illustrate the overall appearance of the new *Petunia* plant showing the colors as true as it is reasonably possible to obtain in colored reproductions of this type. Colors in the photographs may differ slightly from the color values cited in the detailed botanical description which accurately describe the colors of the new *Petunia* plant.

The photograph at the top of the sheet comprises a side perspective view of a typical flowering plant of 'Sunsurf Suika' grown in a container.

The photograph at the bottom of the sheet is a close-up view of a typical flowering plant of 'Sunsurf Suika'.

DETAILED BOTANICAL DESCRIPTION

The aforementioned photographs and following observations, measurements and values describe plants grown during the early summer in 15-cm containers in an outdoor nursery in Higashiomi, Shiga, Japan and under cultural practices typical of commercial *Petunia* production. During the production of the plants, day temperatures averaged 23° C. and night temperatures averaged 13° C. Plants were four months old when the photographs and description were taken. In the following description, color references are made to The Royal Horticultural Society Colour Chart, 2007 Edition, except where general terms of ordinary dictionary significance are used.

Botanical classification: *Petunia×hybrida* 'Sunsurf Suika'.

Parentage:

*Female, or seed, parent*.—Proprietary selection of *Petunia×hybrida* identified as code name Px5306-02, not patented.

*Male, or pollen, parent*.—Proprietary selection of *Petunia×hybrida* identified as code name Px5313-02, not patented.

Propagation:

*Type*.—By terminal cuttings.

*Time to initiate roots, summer and winter*.—About one week at temperatures of about 15° C. to 20° C.

*Time to produce a rooted young plant, summer and winter*.—About three weeks at temperatures of about 15° C. to 20° C.

*Root description*.—Fibrous; white in color.

*Rooting habit*.—Freely branching; dense.

Plant description:

*Plant and growth habit*.—Compact, mounding to trailing plant habit; freely branching habit with numerous lateral branches developing per plant; pinching enhances lateral branch development; vigorous growth habit.

*Plant height*.—About 17.4 cm.

*Plant diameter*.—About 50.5 cm.

Lateral branch description:

*Length*.—About 26 cm.

*Diameter*.—About 3 mm.

*Internode length*.—About 2 cm.

*Strength*.—Strong, flexible.

*Aspect*.—Semi-upright to outwardly.

*Texture*.—Densely pubescent.

*Color*.—Close to 144C.

Foliage description:

*Arrangement*.—Alternate, simple.

*Length*.—About 3 cm.

*Width*.—About 1.3 cm.

*Shape*.—Elliptic.

*Apex*.—Broadly acute.

*Base*.—Attenuate.

*Margin*.—Entire; slightly undulate.

*Texture, upper and lower surfaces*.—Pubescent.

*Venation pattern*.—Pinnate; reticulate.

*Color*.—Developing leaves, upper surface: Close to 143A. Developing leaves, lower surface: Close to 143C. Fully expanded leaves, upper surface: Close to 137B; venation, close to 138B. Fully expanded leaves, lower surface: Close to 137D; venation, close to 144C.

*Petioles*.—Length: About 2.1 mm. Diameter: About 0.5 mm. Texture, upper and lower surfaces: Pubescent. Color, upper and lower surfaces: Close to 144B.

Flower description:

*Flower arrangement and habit*.—Single salverform flowers arising from upper leaf axils; freely flowering habit with usually about 63 flowers developing per plant; flowers face upright to outwardly.

*Fragrance*.—None detected.

*Natural flowering season*.—Early flowering habit, plants of the new *Petunia* initiate and develop flowers about three to four weeks after planting; long flowering period; flowering commences naturally during the spring and plants flower continuously throughout the summer until late autumn in Japan.

*Flower longevity*.—Individual flowers last about seven to ten days on the plant; flowers not persistent.

*Flower diameter*.—About 5.3 cm.

*Flower length (depth)*.—About 3.7 cm.

*Throat diameter*.—About 1.4 cm.

*Tube diameter, base*.—About 3.8 mm.

*Tube length*.—About 2.8 cm.

*Flower buds*.—Length: About 2.8 cm. Diameter: About 6.2 mm. Shape: Cylindrical. Color: Close to 144C.

*Corolla*.—Arrangement: Five petals fused at the base and opening into a flared trumpet. Petal length from throat: About 2.1 cm. Petal width: About 2.5 cm. Petal shape: Spatulate. Petal apex: Mucronate. Petal margin: Entire, undulate. Petal texture, upper and lower surfaces: Coarse, bullate; glabrous. Throat texture: Smooth, glabrous. Tube texture: Densely pubescent.

Color: Petal, when opening, upper surface: Close to 64C; margins, close to 144A; venation, close to 64B. Petal, when opening, lower surface: Close to 65A; margins and venation, close to 144A. Petal, fully opened, upper surface: Close to 68A; margins, close to 144A; venation, close to 64B. Petal, fully opened, lower surface: Close to 65C; margins and venation, close to 144A. Throat: Close to 145D; venation, close to N77B. Tube: Close to 145D; venation, close to 144A.

*Calyx*.—Arrangement: One star-shaped calyx tube with five sepals in a single whorl and fused at the base. Sepal length: About 1.7 cm. Sepal width: About 4.5 mm. Sepal shape: Narrowly elliptic. Sepal apex: Obtuse. Sepal margin: Entire. Sepal texture, upper and lower surfaces: Pubescent. Color: Developing and fully opened sepals, upper surface: Close to 143B. Developing and fully opened sepals, lower surface: Close to 143C.

*Peduncles*.—Length: About 2.4 cm. Diameter: About 1.6 mm. Strength: Strong. Texture: Densely pubescent. Color: Close to 143B.

*Reproductive organs*.—Stamens: Quantity per flower: Five. Stamen length: About 1.6 cm to 2 cm. Anther shape: Ovoid.. Anther size: About 2.1 mm by 3.3 mm. Anther color: Close to 4C. Pollen amount: Moderate. Pollen color: Close to 4C. Pistils: Quantity per flower: One. Pistil length: About 2 cm. Style color: Close to 145B. Stigma shape: Transversely ellipsoidal. Stigma color: Close to 150B. Ovary color: Close to 145B. Seeds and fruits: Seed and fruit development have not been observed on plants of the new *Petunia*.

Garden performance: Plants of the new *Petunia* have been observed to have good garden performance and to tolerate rain, wind and temperatures ranging from about 5° C. to about 35° C.

Pathogen & pest resistance: Plants of the new *Petunia* have not been observed to be resistant to pathogens and pests common to *Petunia* plants.

It is claimed:

1. A new and distinct *Petunia* plant named 'Sunsurf Suika' as illustrated and described.

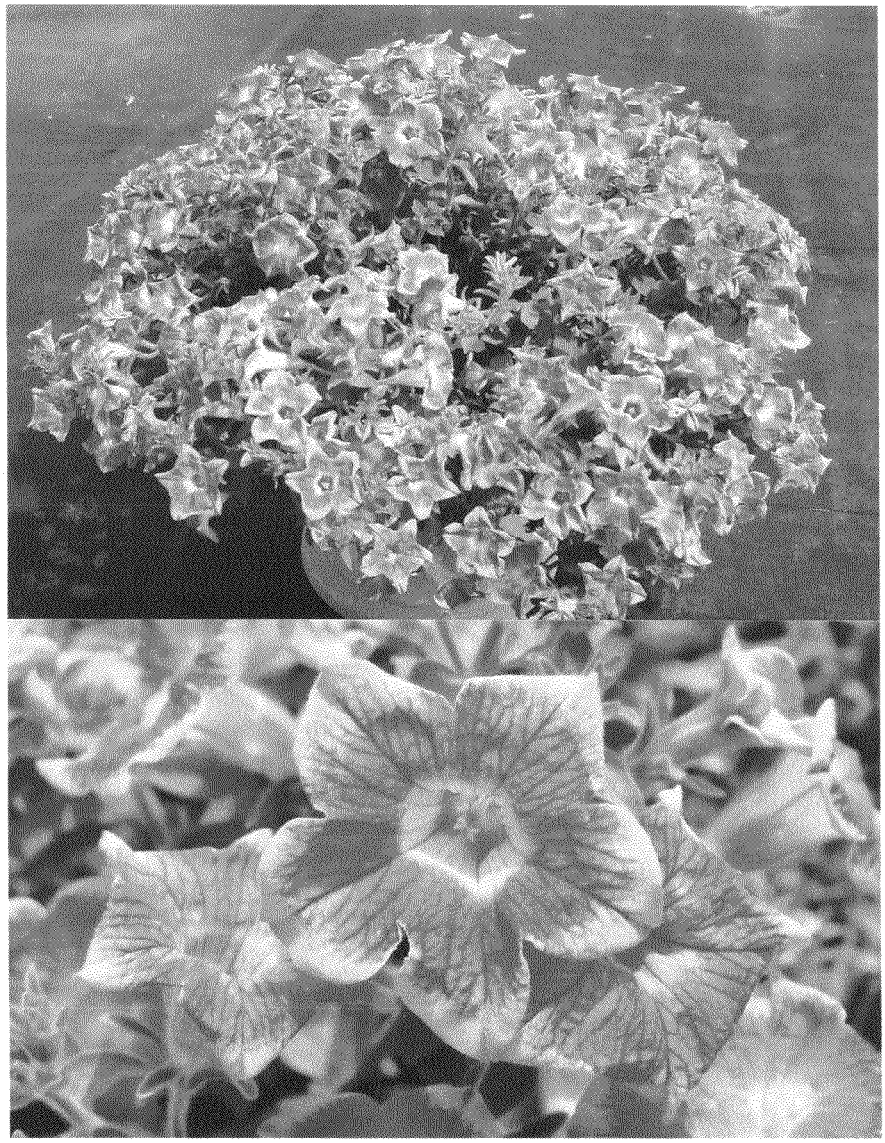

* * * * *